US011426113B2

(12) United States Patent
Perumalla et al.

(10) Patent No.: US 11,426,113 B2
(45) Date of Patent: Aug. 30, 2022

(54) SYSTEM AND METHOD FOR THE PREDICTION OF ATRIAL FIBRILLATION (AF)

(71) Applicant: University of South Florida, Tampa, FL (US)

(72) Inventors: Calvin Apollos Perumalla, Tampa, FL (US); Richard Dennis Gitlin, Tampa, FL (US); Dilranjan Sunimal Wickramasuriya, Houston, TX (US)

(73) Assignee: University of South Florida, Tampa, FL (US)

( * ) Notice: Subject to any disclaimer, the term of this patent is extended or adjusted under 35 U.S.C. 154(b) by 72 days.

(21) Appl. No.: 16/804,941

(22) Filed: Feb. 28, 2020

(65) Prior Publication Data

US 2020/0196886 A1    Jun. 25, 2020

Related U.S. Application Data

(63) Continuation of application No. PCT/US2018/048331, filed on Aug. 28, 2018.

(60) Provisional application No. 62/550,874, filed on Aug. 28, 2017.

(51) Int. Cl.
```
A61B 5/361      (2021.01)
G16H 40/67      (2018.01)
G16H 50/30      (2018.01)
A61B 5/316      (2021.01)
A61B 5/341      (2021.01)
A61B 5/352      (2021.01)
A61B 5/363      (2021.01)
```

(52) U.S. Cl.
CPC ............. *A61B 5/361* (2021.01); *A61B 5/316* (2021.01); *A61B 5/341* (2021.01); *A61B 5/352* (2021.01); *A61B 5/363* (2021.01); *G16H 40/67* (2018.01); *G16H 50/30* (2018.01)

(58) Field of Classification Search
CPC ......... A61B 5/361; A61B 5/316; A61B 5/341; A61B 5/352; A61B 5/363; G16H 40/67; G16H 50/30
See application file for complete search history.

(56) References Cited

U.S. PATENT DOCUMENTS

2005/0027331 A1    2/2005 Bardy

OTHER PUBLICATIONS

Arotaritei, D. et al., Automatic Prediction of Paroxysmal Atrial Fibrillation in Patients with Heart Arrhythmia, 2014 International Conference and Exposition on Electrical and Power Engineering (EPE 2014), Oct. 16-18, Iasi, Romania, pp. 549-552.
Arrobo, G. E. et al., A Novel Vectorcardiogram System, Proc. IEEE Int. Conf. e-Health, Net. Appl. Serv., Oct. 2014, pp. 188-192.
De Chazal, P. et al., Automated Assessment of Atrial Fibrillation, Comput. Cardiol. 2001, vol. 28, pp. 117-120, 2001.
Chesnokov, Y. V. et al., Distant Prediction of Paroxysmal Atrial Fibrillation Using HRV Data Analysis, Comput. Cardiol. 2007, vol. 34, pp. 455-458, 2007.

(Continued)

*Primary Examiner* — Mallika D Fairchild
*Assistant Examiner* — Shreya Anjaria
(74) *Attorney, Agent, or Firm* — Smith & Hopen, P.A.; Molly L. Sauter

(57) ABSTRACT

System and method for providing patient-specific models to distinguish between epochs of electrocardiograms (ECGs) located far away from atrial fibrillation rhythms and those located just prior to the onset of those episodes, to provide for the prediction of the onset of an occurrence of atrial fibrillation (AF) in the patient.

18 Claims, 6 Drawing Sheets

(56) References Cited

OTHER PUBLICATIONS

Das, R. et al., Effective diagnosis of heart disease through neural networks ensembles, Expert Systems with Applications 36 (2009) 7675-7680.
Feinberg, W. M. et al., Prevalence, Age Distribution, and Gender of Patients with Atrial Fibrillation, Arch. Intern. Med., vol. 155, pp. 469-473, Mar. 1995.
Goldberger, A. L. et al., PhysioBank, PhysioToolkit, and PhysioNet Components of a New Research Resource for Complex Physiologic Signals, Circulation, vol. 101, pp. e215-e220, Jun. 2000.
Hall, M. et al., The WEKA Data Mining Software: An Update, SIGKDD Explor. Newsl., vol. 11, pp. 10-18, Nov. 2009.
Chhabbi, A. et al., Heart Disease Prediction Using Data Mining Techniques, International Journal of Research in Advent Technology (E-ISSN: 2321-9637) Special Issue National Conference "NCPCI-2016", Mar. 19, 2016, pp. 104-106.
Hilavin, I. et al., Prediction of Paroxysmal Atrial Fibrillation Onset by Using ECG, Proc. Int. Symp. Inno. Int. Sys. Appl., Jul. 2012, pp. 1-3.
Hnatkova, K. et al., Analysis of the cardiac rhythm preceding episodes of paroxysmal atrial fibrillation, Am. Heart J., vol. 131, No. 6, pp. 1010-1019, Jun. 1998.
Parthiban, L. et al., Intelligent Heart Disease Prediction System using CANFIS and Genetic Algorithm, International Journal of Biological and Medical Sciences 3:3 2008, pp. 157-160.
Palaniappan, S. et al., Intelligent Heart Disease Prediction System Using Data Mining Techniques, IJCSNS International Journal of Computer Science and Network Security, vol. 8 No. 8, Aug. 2008, pp. 343-350.
Langley, P. et al., Can Paroxysmal Atrial Fibrillation Be Predicted? Comput. Cardiol. 2001, vol. 28, pp. 121-124, 2001.
Lindsberg, P. J. et al., The atrial fibrillation epidemic is approaching the physician's door: will mobile technology improve detection? BMC Medicine 2014, 12:180.
Lynn, K. S. et al., A two-stage solution algorithm for paroxysmal atrial fibrillation prediction, Comput. Cardiol. 2001, vol. 28, pp. 405-407, 2001.
Maier, C. et al., Screening and prediction of paroxysmal atrial fibrillation by analysis of heart rate variability parameters, Comput. Cardiol. 2001, vol. 28, pp. 129-132, 2001.
Mann, H. B. et al., On a Test of Whether One of Two Random Variables is Stochastically Larger Than the Other, The Annals of Mathematical Statistics, vol. 18, No. 1 (Mar. 1947), pp. 50-60.
Moody, G. B. et al., Predicting the Onset of Paroxysmal Atrial Fibrillation: The Computers in Cardiology Challenge 2001, Comput. Cardiol. 2001, vol. 28, pp. 113-116, 2001.
Wickramasuriya, D. S. et al., Predicting Episodes of Atrial Fibrillation using RR-Intervals and Ectopic Beats, 2017 IEEE EMBS International Conference on Biomedical & Health Informatics (BHI). Feb. 19, 2017.
Padmavathi, K. et al., Classification of ECG signal during Atrial Fibrillation using Autoregressive modeling, International Conference on Information and Communication Technologies (ICICT2014), Procedia Computer Science 46 ( 2015 ) 53-59.
Pertrutiu, S. et al., Abrupt changes in fibrillatory wave characteristics at the termination of paroxysmal atrial fibrillation in humans, Europace (2007) 9, 466-470.
Soni, J. et al., Predictive Data Mining for Medical Diagnosis: An Overview of Heart Disease Prediction, International Journal of Computer Applications (0975-8887), vol. 17—No. 8, Mar. 2011, pp. 43-48.
Schreier, G. et al., An automatic ECG processing algorithm to identify patients prone to paroxysmal atrial fibrillation, Comput. Cardiol. 2001, vol. 28, pp. 133-135, 2001.
Thong, T. et al., Prediction of Paroxysmal Atrial Fibrillation by Analysis of Atrial Premature Complexes, IEEE Transactions on Biomedical Engineering, vol. 51, No. 4, Apr. 2004, pp. 561-569.
Wolf, P. A. et al., Impact of Atrial Fibrillation on Morality, Stroke, and Medical Costs, Arch Intern Med. 1998; 158:229-234.
Zong, W. et al., A Methodology for Predicting Paroxysmal Atrial Fibrillation Based on ECG Arrhythmia Feature Analysis, Comput. Cardiol. 2001, vol. 28, pp. 125-128, 2001.
International Search Report and Written Opinion dated Nov. 2, 2018 for PCT International Application No. PCT/US2018/048331.
International Preliminary Report on Patentability dated Mar. 12, 2020 for PCT International Application No. PCT/US2018/048331.

SYSTEM AND METHOD FOR THE PREDICTION OF ATRIAL FIBRILLATION (AF)

CROSS-REFERENCE TO RELATED APPLICATIONS

This application is a continuation of and claims priority to PCT International Application No. PCT/US2018/048331, entitled "SYSTEM AND METHOD FOR THE PREDICTION OF ATRIAL FIBRILLATION (AF)," filed Aug. 28, 2018, which claims priority to U.S. Provisional Patent Application No. 62/550,874, entitled "Prediction of Heart Disease Using an Integrated Vector Cardiogram System," filed Aug. 28, 2017, the entirety of each are incorporated herein by reference.

BACKGROUND OF THE INVENTION

1. Field of the Invention

The disclosed embodiments relate generally to computing devices, and in particular, to computing devices and computer-implemented methods for personalized prediction of heart disease, such as atrial fibrillation (AF).

2. Brief Description of the Prior Art

Atrial fibrillation (AF) is the most common cardiac arrhythmia and is characterized by the heart's inability to contract effectively. AF is associated with an increased risk of embolic stroke and mortality, which affects more than 2.2 million people in the United States. AF may be classified as paroxysmal, persistent, or permanent, based on the duration of the fibrillatory rhythms. In the paroxysmal case, in particular, intermittent AF episodes occur and terminate on their own, thus potentially putting patients at risk of being undiagnosed with the arrhythmia. Research into the prediction of AF onset has been motivated by the necessity to develop better pacing therapy to reduce the incidence of AF and maintain the heart's normal sinus rhythm.

Accordingly, what is needed is a system and method to predict the onset of episodes of AF so that better pacing therapies can be developed to maintain the heart's normal sinus rhythm. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

SUMMARY OF THE INVENTION

In various embodiments the present invention provides a system and method for predicting the onset of an atrial fibrillation (AF) event in a patient of interest.

In one embodiment, the present invention provides a method for predicting the onset of an AF event. The method can be implemented in one or more computing devices comprising one or more hardware processors and memory storing one or more computer programs executed by the one or more hardware processors. The method includes, identifying one or more AF (atrial fibrillation) rhythms in historical ECG data of a patient, distinguishing between one or more distant-AF (atrial fibrillation) ECG epochs in the historical ECG data and one or more pre-AF ECG epochs in the historical data, wherein the distant-AF ECG epochs are located far away from the one or more AF rhythms in the historical ECG data and wherein the pre-AF ECG epochs are located just prior to the onset of the one or more AF rhythms in the historical ECG data and establishing a baseline for the patient based upon the one or more pre-AF ECG epochs and the one or more distant-AF ECG epochs. The method further includes, monitoring current electrical activity of the patient's heart using an electrical activity heart monitoring device and comparing the current electrical activity of the patient's heart to the baseline established for the patient to predict an onset of AF in the patient.

Distinguishing between one or more distant-AF (atrial fibrillation) ECG epochs in the historical ECG data and one or more pre-AF ECG epochs in the historical data is accomplished by identifying a plurality of distinguishing features in the historical ECG data, wherein the plurality of distinguishing features in the historical ECG data identify variations in the patient's heart rate from the historical ECG data.

Identifying a plurality of distinguishing features may further include, identifying the one or more distant-AF ECG epochs in the historical ECG data and identifying the one or more pre-AF ECG epochs in the historical ECG data. Following the identification of the distant-AF and pre-AF ECG epochs, the method may further include, utilizing heart beat annotations in the one or more distant-AF epochs to extract one or more distant-AF RR-interval time series from the one or more distant-AF ECG epochs and subtracting a cubic spline interpolated trend line from the distant-AF RR-interval time series to center the RR-interval time series about zero to generate a normalized distant-AF RR-interval time series and utilizing heart beat annotations in the one or more pre-AF epochs to extract one or more pre-AF RR-interval time series from the one or more pre-AF epochs and subtracting a cubic spline interpolated trend line from the pre-AF RR-interval time series to center the pre-AF RR-interval time series about zero to generate a normalized pre-AF RR-interval time series. Using the normalized pre-AF RR-interval time series and the normalized distant-AF RR-interval time series, the method may further include, identifying distinguishing features in the one or more distant-AF RR-interval time series comprising, a number of outliers, a maximum, a minimum, a mean and a median and identifying distinguishing features in the one or more normalized distant-AF RR-interval time series comprising, a number of outliers, a maximum, a minimum, a mean and a median.

Additionally, identifying a plurality of distinguishing features may further include, utilizing heart beat annotations in the one or more distant-AF epochs to extract one or more distant-AF RR-interval time series from the one or more distant-AF ECG epochs and to extract one or more pre-AF RR-interval time series from the one or more pre-AF epochs. Following the extraction of the distant-AF ECG RR-interval time series and the pre-AF ECG RR-interval time series, the method may further include, extracting one or more outliers from the one or more distant-AF RR-interval time series and extracting one or more outliers from the one or more pre-AF RR-interval time series. Following the extraction of the one or more outliers, the method may further include, identifying distinguishing features of the one or more distant-AF RR-interval time series without the one or more outliers comprising, a median and a root mean square value and identifying distinguishing features of the one or more pre-AF RR-interval time series without the one or more outliers comprising, a median and a root mean square value.

In addition, identifying distinguishing features may further include, utilizing heart beat annotations in the one or more distant-AF epochs to extract one or more distant-AF RR-interval time series from the one or more distant-AF ECG epochs and to extract one or more pre-AF RR-interval time series from the one or more pre-AF epochs. Following the extraction of the distant-AF RR-interval time series and the pre-AF RR-interval time series, the method may further include, identifying distinguishing features comprising autoregressive coefficients that capture a variation within the distant-AF RR-interval time series and within the pre-AF RR-interval time series.

Identifying a plurality of distinguishing features may further include, identifying one or more abnormal heart beats or abnormal heart rhythm changes in the historical ECG data and identifying distinguishing features comprising a number of abnormal heart beats or abnormal heart rhythm changes. The abnormal heart beats may be selected from premature atrial contractions and premature ventricular contractions. The abnormal heart rhythm changes may be selected from sinus bradycardia, ventricular tachycardia, atrial bigeminy, supraventricular tachycardia and ventricular bigeminy.

As such, in an exemplary method of the present invention, the plurality of distinguishing features in the historical ECG data are selected from a feature vector comprising twenty-seven values for each pre-AF ECG epoch and each distant-AF ECP epoch using a ranksum test resulting in four distinguishing features that are used to distinguish pre-AF epochs from distant-AF epochs, resulting in a baseline for the patient. The baseline is then used to predict an AF event when continuous monitoring of the patient's heart is being performed. In a specific embodiment, monitoring the current electrical activity of the patient's heart maybe performed by an embedded vectorcardiogram device.

In an additional embodiment, the present invention provides a system for predicting the onset of AF in a patient. The system may include, analog processing circuitry and associated memory for, identifying one or more AF (atrial fibrillation) rhythms in historical ECG data of a patient, distinguishing between one or more distant-AF (atrial fibrillation) ECG epochs in the historical ECG data and one or more pre-AF ECG epochs in the historical data, wherein the distant-AF ECG epochs are located far away from the one or more AF rhythms in the historical ECG data and wherein the pre-AF ECG epochs are located just prior to the onset of the one or more AF rhythms in the historical ECG data, establishing a baseline for the patient based upon the one or more pre-AF ECG epochs and the one or more distant-AF ECG epochs, monitoring current electrical activity of the patient's heart using an electrical activity heart monitoring device and comparing the current electrical activity of the patient's heart to the baseline established for the patient to predict an onset of AF in the patient.

In another embodiment, the present invention provides one or more tangible non-transitory computer-readable media having computer-executable instructions for performing a method of running a software program on a computing device, the computing device operating under an operating system, the method including issuing instructions from the software program, wherein the media includes instructions for, identifying one or more AF (atrial fibrillation) rhythms in historical ECG data of a patient, distinguishing between one or more distant-AF (atrial fibrillation) ECG epochs in the historical ECG data and one or more pre-AF ECG epochs in the historical data, wherein the distant-AF ECG epochs are located far away from the one or more AF rhythms in the historical ECG data and wherein the pre-AF ECG epochs are located just prior to the onset of the one or more AF rhythms in the historical ECG data, establishing a baseline for the patient based upon the one or more pre-AF ECG epochs and the one or more distant-AF ECG epochs, monitoring current electrical activity of the patient's heart using an electrical activity heart monitoring device and comparing the current electrical activity of the patient's heart to the baseline established for the patient to predict an onset of AF in the patient.

Accordingly, the present invention provides a system and method for predicting the onset of AF in a patient of interest which may be implemented in a continuous monitoring device.

BRIEF DESCRIPTION OF THE DRAWINGS

For a fuller understanding of the invention, reference should be made to the following detailed description, taken in connection with the accompanying drawings, in which.

DETAILED DESCRIPTION OF THE INVENTION

In the following detailed description of the preferred embodiments, reference is made to the accompanying drawings, which form a part thereof, and within which are shown by way of illustration specific embodiments by which the invention may be practiced. It is to be understood that other embodiments may be utilized, and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

A vectorcardiogram device, such as the device described in U.S. Pat. No. 9,451,890 developed by the current inventors, is an integrated heart signal monitoring device providing full-diagnostic quality and remote long-term monitoring. The inventive device has the ability to compensate for errors induced when placed incorrectly on a patient's chest and has wireless connectivity to a user's smart phone. Accumulating continuous heart signal recordings (i.e. "big data") better equips healthcare providers to monitor patients remotely, thereby helping them to avoid unnecessary hospital visits and to open up the possibility of developing algorithms tailored to each patient (i.e., personalized) to predict impending cardiac events. The necessity for long-term monitoring for diagnosing infrequent paroxysmal AF is known, as is the need for automated event detection, especially if episodes are asymptomatic.

In various embodiments, the current invention is a method that predicts a heart condition based on data obtained by suitable electrocardiogram monitoring devices. The prediction techniques provided by the present invention may be generally applied to any heart condition, such as paroxysmal atrial fibrillation (PAF), which will be discussed herein in a non-limiting example. In one exemplary embodiment, the current invention takes as input a wireless ECG input or an integrated vectorcardiogram input, and through the use of two machine learning techniques, known as the neural networks and support vector machines, outputs an accurate prediction regarding whether or not a PAF episode is imminent.

In an exemplary embodiment for predicting episodes of atrial fibrillation using RR-intervals and ectopic beats, presented herein is a patient-specific approach to predicting the occurrence of impending episodes of AF, and this approach is validated using a publicly available dataset. An overview of the general methodology can be seen in FIG. 1.

Figure 1:
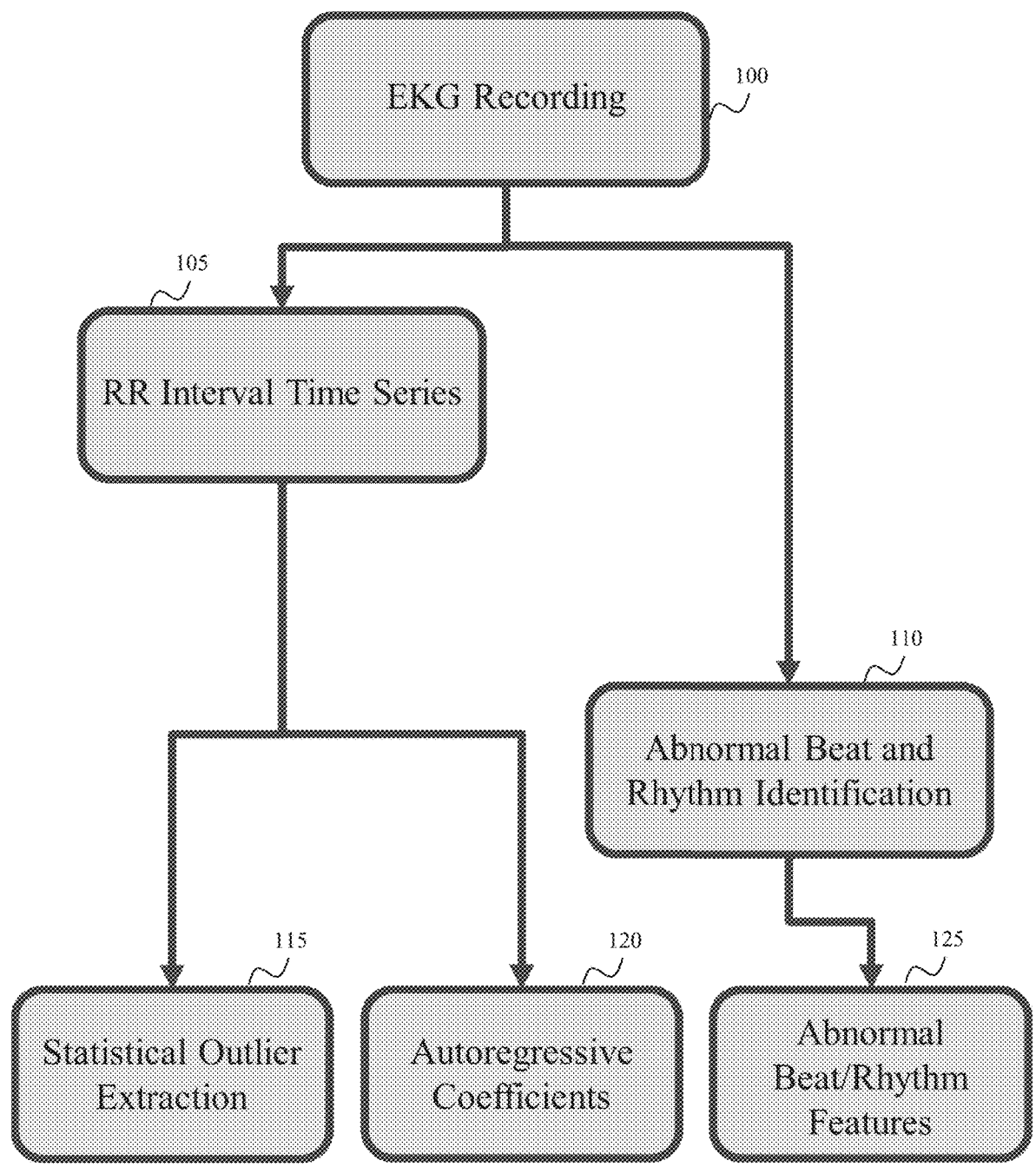
FIG. 1 is a flowchart depicting a general methodology for obtaining and processing historical ECG data, according to an embodiment of the present invention.

As shown in FIG. 1, in a broad exemplary embodiment of the present invention, the recorded ECG (electrocardiogram) data 100 of a patient of interest is provided from a heart signal detection device. The pre-AF RR-interval time series data and the distant-AF RR-interval time series data are then extracted from the ECG data 105 and abnormal beats and rhythms are identified in the ECG data 110. Statistical outliers are then identified and removed from the RR-interval time series data 115 and distinguishing features are extracted from the RR-interval time series data. The abnormalities are used to provide additional distinguishing features 125. Autoregressive coefficients that capture a variation within the distant-AF RR-interval time series and within the pre-AF RR-interval time series are also identified 120 and incorporated into the distinguishing features. The distinguishing features provided by the method of the invention are then used to distinguish distant-AF epochs from pre-AF epochs in the historical ECG data of the patient and to create a baseline for the prediction of AF events. By continually monitoring the heart signals of the patient, the baseline can be used to detect the onset of AF event in the patient of interest.

In this exemplary embodiment, data was obtained from the Long-Term Atrial Fibrillation Database (LTAFDB) from PhysioBank. PhysioBank is a large and growing archive of well-characterized digital recordings of physiologic signals and related data for use by the biomedical research community. PhysioBank currently includes databases of multi-parameter cardiopulmonary, neural, and other biomedical signals from healthy subjects and patients with a variety of conditions with major public health implications, including sudden cardiac death, congestive heart failure, epilepsy, gait disorders, sleep apnea, and aging.

The PhysioBank data used in this exemplary embodiment included 84 ECG recordings from patients with sustained or paroxysmal AF. Each recording was approximately 24 hours in duration and contained two ECG signals recorded at a sampling frequency of 128 Hz. For the purpose of this study, ECGs that occurred shortly before the commencement of episodes of AF needed to be distinguished from ECG signals that were sufficiently far away from such abnormal rhythms.

For each recording, the 2-minute ECG epoch prior to each AF episode was extracted. This was labeled as the pre-AF set. One hundred (100) ECG epochs were randomly selected, each being two (2) minutes in duration, from every recording, located at least 10 minutes away from an AF rhythm. This collection of ECGs was labeled as the normal or distant set. This procedure was repeated for each patient.

Thereafter, ECG epochs of identical duration (2 minutes) were selected from the same records, but with each of the ECG epochs terminating at 0, 1, 2, and 3 minutes, respectively, prior to the start of each episode of AF, and they were labeled as the pre-atrial fibrillation (pre-AF) set. If an epoch contained another AF episode, it was discarded. Only recordings containing at least 20 episodes of AF were selected in order to have enough data for both classes to train patient-specific models.

Figure 2A:
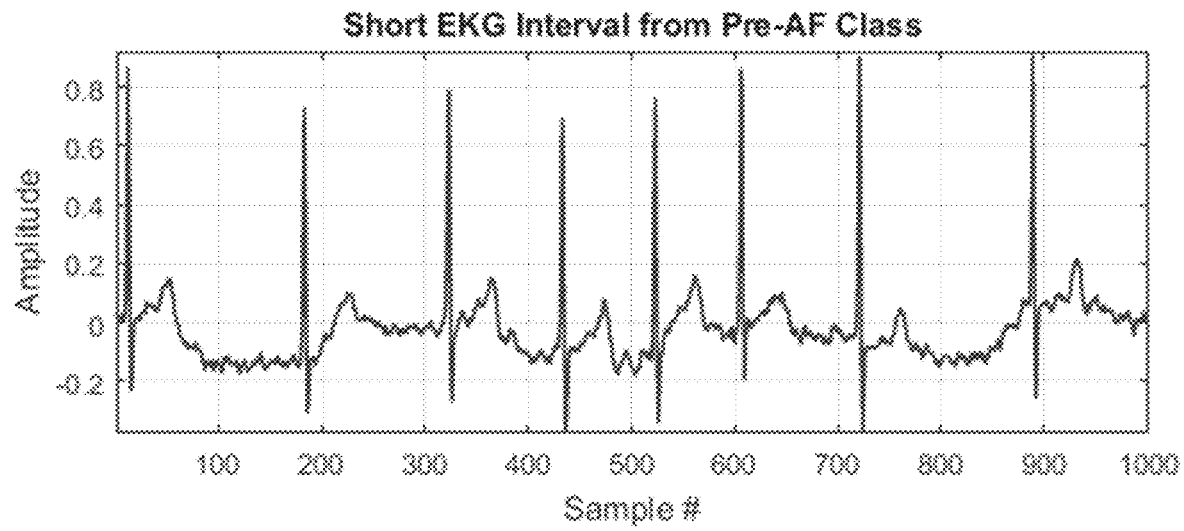
FIG. 2A depicts ECGs for pre-AF ECG historical data.
Figure 2B:
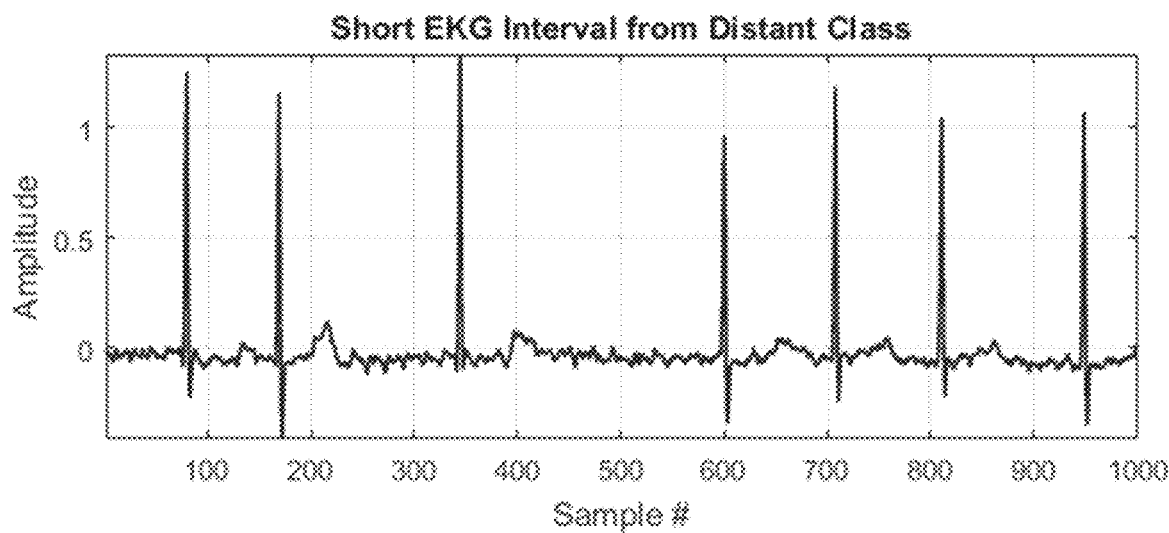
FIG. 2B depicts ECGs for distant-ECG historical data.

In feature extraction from the ECG data, generally, features were chosen to distinguish between pre-AF ECG epochs and ECG epochs far away from AF episodes. Example ECGs belonging to both classes can be seen in FIG. 2A and FIG. 2B, wherein FIG. 2A illustrates pre-AF ECG epochs and FIG. 2B illustrates distant-AF ECG epochs.

Figure 3:
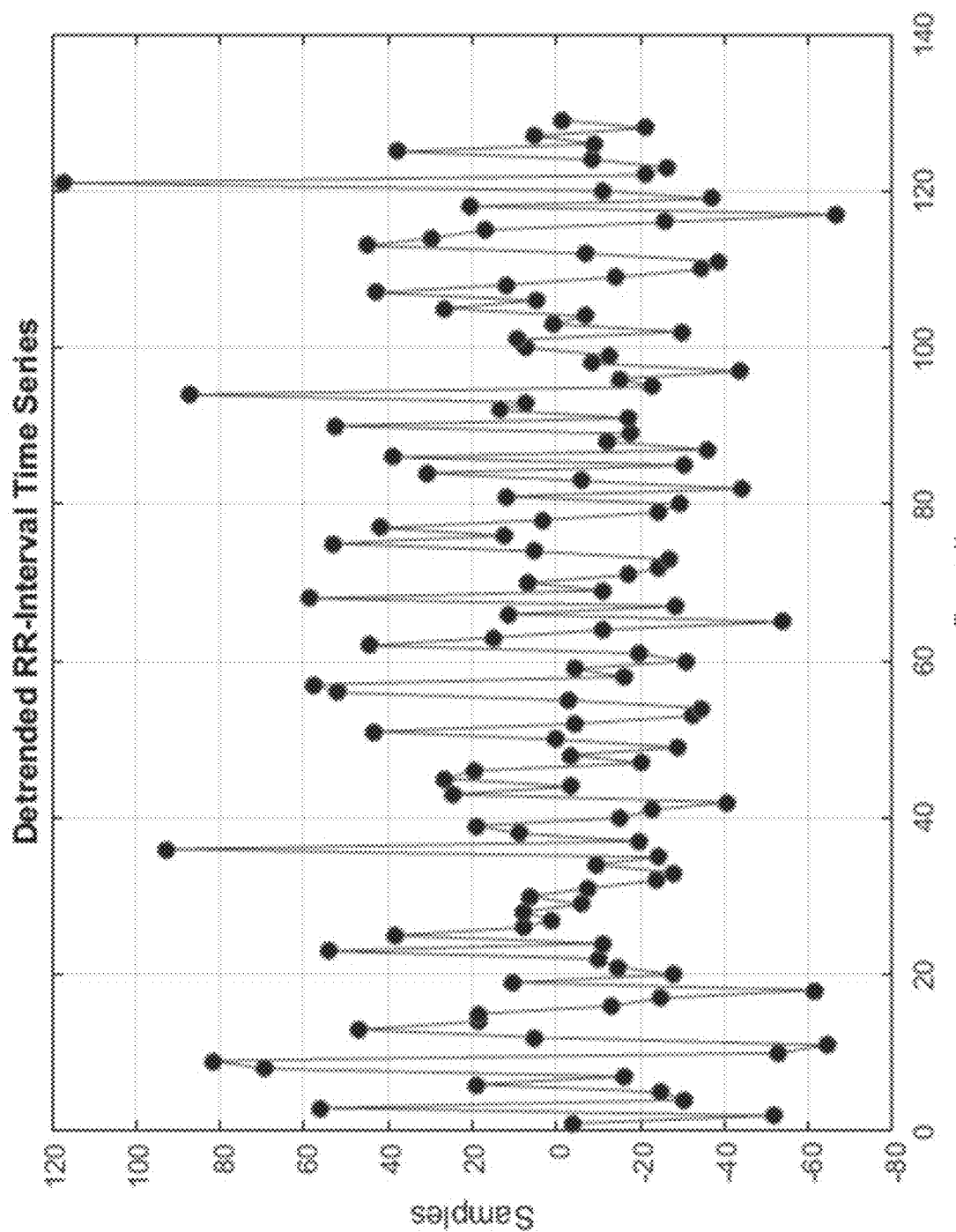
FIG. 3 depicts an example detrended RR-intervals series.

More specifically, beat annotations provided in the data from the LTAFDB were used to extract RR-interval time series from the ECGs. In an electrocardiogram, the interval from the onset of one R wave to the onset of the next one, which comprises one complete cardiac cycle, is referred to as an RR-interval. A cubic spline interpolated trend line was subtracted from these series to center them about zero. The RR-interval data was manually inspected to identify good features that were correlated with the target class. An example detrended RR-interval series is shown in FIG. 3.

Eight statistics were chosen to characterize variations in heart rate during each 2-minute interval. After normalizing the data by dividing by the maximum absolute value, outliers were defined as the points greater than three standard deviations away from zero. The number of outliers, their maximum, minimum, mean, and median were the first five statistics calculated from the normalized time series. Next, the median and root mean square value of the series without the outliers were also extracted. Finally, the length of the series (i.e., the number of data points in the series that is equivalent to the number of heartbeats during the epoch) was extracted. Additionally, four autoregressive (AR) coefficients were extracted herein as further descriptors of HRV and to capture the variation within the RR-interval time series.

Annotations accompanying the original ECG signals indicate locations where abnormal heart beats and abnormal rhythm changes occurred. The most frequently appearing abnormal beat types include premature atrial contractions and premature ventricular contractions, while sinus bradycardia, ventricular tachycardia, atrial bigeminy, supraventricular tachycardia and ventricular bigeminy are among some of the abnormally occurring rhythms. The number of these individual types of beats and rhythms occurring in each epoch were also incorporated into the features. When concatenated, all of the above attributes form a feature vector with 27 features/values corresponding to each 2-minute ECG epoch.

In a particular embodiment, a Mann-Whitney ranksum test was used to select the best features that distinguish between the subset of ECG epochs belonging to distant-AF class and the subset of ECG epochs belonging to the pre-AF class, which terminate right at the commencement of an episode (i.e., 0 minutes before the onset of fibrillatory rhythm) for each patient. The Mann-Whitney ranksum test indicates whether the particular feature of the 27 features being considered are distributed with different medians for each class. Features for which the p-value was less than 0.05 were selected to perform classification. Then, ranksum tests were repeated for the remaining subsets of ECGs terminating 1, 2, and 3 minutes prior to the AF episodes to select the best set of features that distinguish each of them from features belonging to the distant-AF set. In total, four separate classifiers were trained for each patient/record. The time between the end of an ECG epoch and the commencement of a fibrillatory rhythm was labeled—being either 0, 1, 2, or 3 minutes—as the prediction horizon.

For classification, support vector machines (SVMs) and neural networks (NN) were selected and evaluated due to their superior accuracy with 10-fold cross-validation. Sensitivity, specificity, and overall accuracy were calculated for each of the four classifiers trained per patient. As such, SVM classification was performed for every patient individually for each prediction horizon, i.e., there were 4 SVMs in all trained for each patient. If any ECG epochs belonging to the pre-AF class contained another AF rhythm within it, it was discarded. Since sufficient data was required to perform SVM classification for each patient, for all 4 prediction horizons (0, 1, 2 and 3 minutes), only records/patients having at least 20 AF episodes were considered and others were discarded.

Classification accuracy was high for patients when classifying between the distant signals and those that terminate just prior to fibrillatory rhythms. The mean accuracy in prediction for this particular prediction horizon was 95.2%.

tivity, after an initial drop, at subsequent stages (corresponding to longer prediction horizons) may indicate a slight overfit on the part of the SVMs.

As such, in the present invention, distinguishing between 2-minute epochs of ECG data occurring just prior to fibrillatory rhythms and those that occur sufficiently further away, provides for patient-specific models for predicting the occurrence of AF episodes. The current method seeks to classify between all the data points belonging to a particular patient at once, rather than merely deciding which ECG occurs just prior to the AF episode when presented with two ECGs at a time. Classification accuracy was high for most patients when classifying between the distant-AF ECG signals and the pre-AF ECG signals that terminated just prior to fibrillatory rhythms. It was found that classification sensitivities are high for small prediction horizons.

Figure 5:
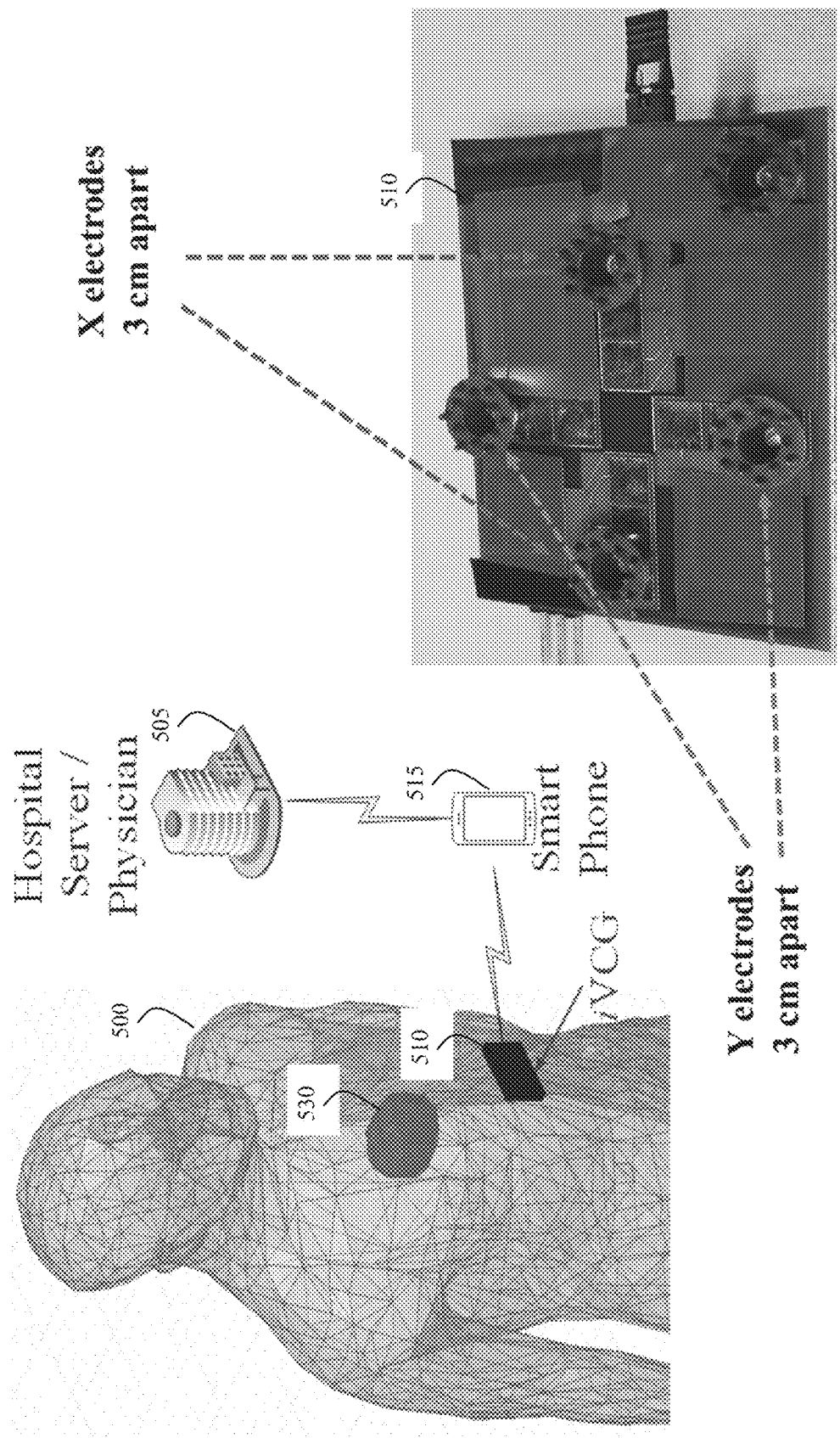
FIG. 5 depicts incorporation of an integrated vectorcardiogram into a methodology or system, according to an embodiment of the present invention.

In a particular implementation, for example, the method of the present invention can be implemented on an embedded device, such as the integrated vectorcardiogram (VCG) monitor shown in U.S. Pat. No. 9,451,890. As shown in FIG. 5, a device for measuring the electrical activity of a heart 530 of a patient 500 may be a miniaturized wireless integrated VCG device 510 and may include a mobile data system 515 such as, but not limited to, a smart phone and an associated server 505. In an additional embodiment, a pacemaker 40 (Cardiac Resynchronization Therapy Device/Implantable Cardioverter Defibrillator) that may be a part of the integrated vectorcardiogram system, which can be controlled by the integrated vectorcardiogram device 510 to regulate the signals to the patient's 500 heart 530. The VCG device 510 may also incorporate artificial intelligence (machine learning) technology, security and device authentication, and wireless communication capabilities. The integrated vectorcardiogram system enables continuous, comprehensive, long-term, information collection from an outpatient, or in an in-hospital patient, that is identical in content to the data available from the office-based 12-lead ECG. The monitoring device could be an IoT (Internet of Things) device capable of warning a caregiver of an impending cardiac event, as shown in FIG. 5.

Figure 6:
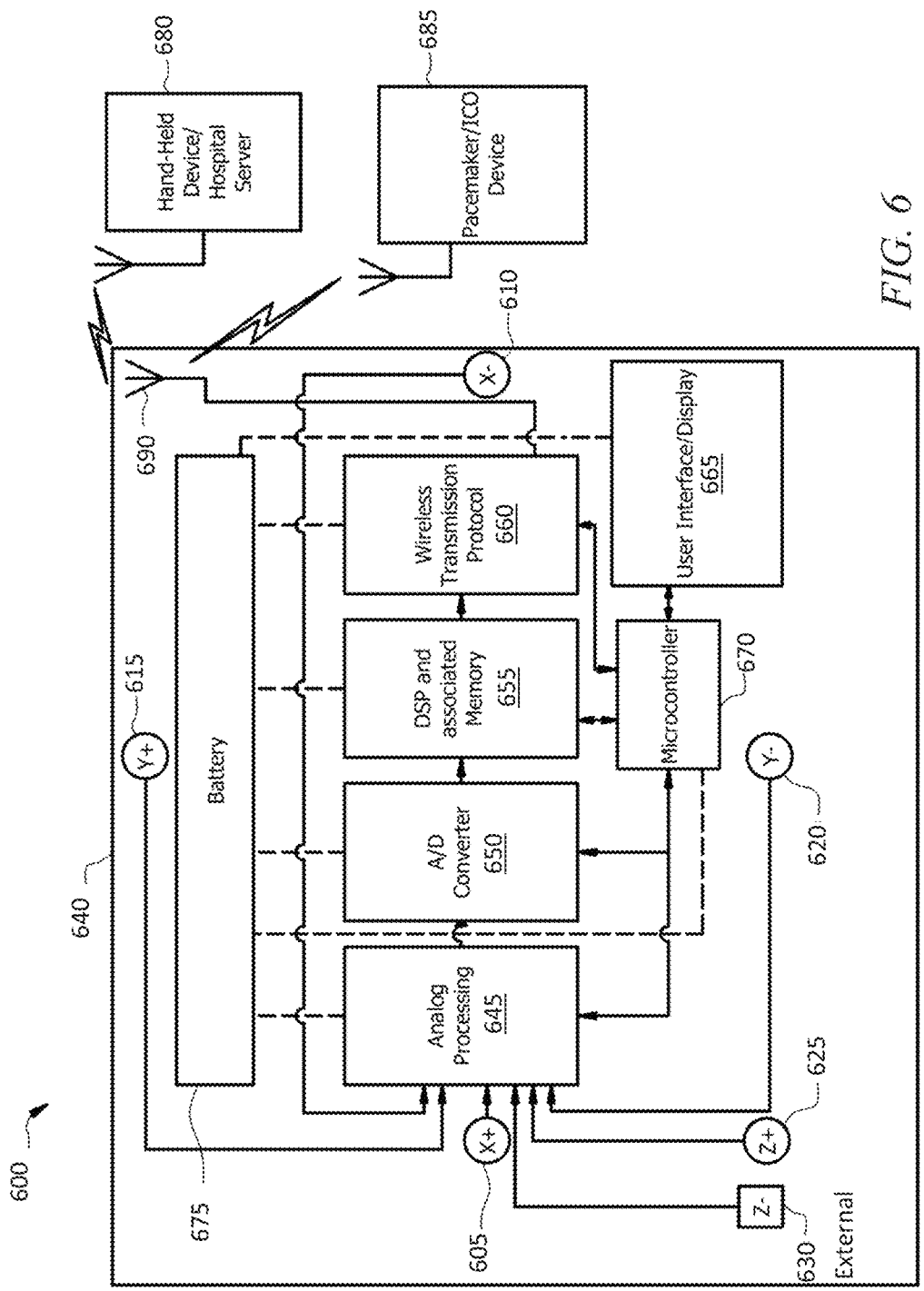
FIG. 6 is a block diagram illustrating the hardware components of a exemplary vectorcardiogram, according to an embodiment of the present invention.

With reference to FIG. 6, a functional block diagram representation of an exemplary external integrated VCG device 600 is illustrated. In this embodiment, "external" is used to refer to an embodiment of the VCG device 60 that is adapted to be positioned in a measurement position on the skin surface of a patient. In this embodiment, the X-axis electrodes 605, 610, the Y-axis electrodes 615, 620 and one of the Z-axis electrodes 625 are integrated into the housing

TABLE 1

Variation of Average Model Accuracy with Prediction Horizon.

| 0 s TO AFIB EPISODE | | | 60 s TO AFIB EPISODE (1 MINUTE) | | | 120 s TO AFIB EPISODE (2 MINUTES) | | |
| --- | --- | --- | --- | --- | --- | --- | --- | --- |
| SPEC. (%) | SENS. (%) | ACC. (%) | SPEC. (%) | SENS. (%) | ACC. (%) | SPEC. (%) | SENS. (%) | ACC. (%) |
| 93.9 | 95.2 | 95.2 | 91.3 | 44.8 | 80.2 | 93.5 | 37.4 | 80.9 |

Figure 4:
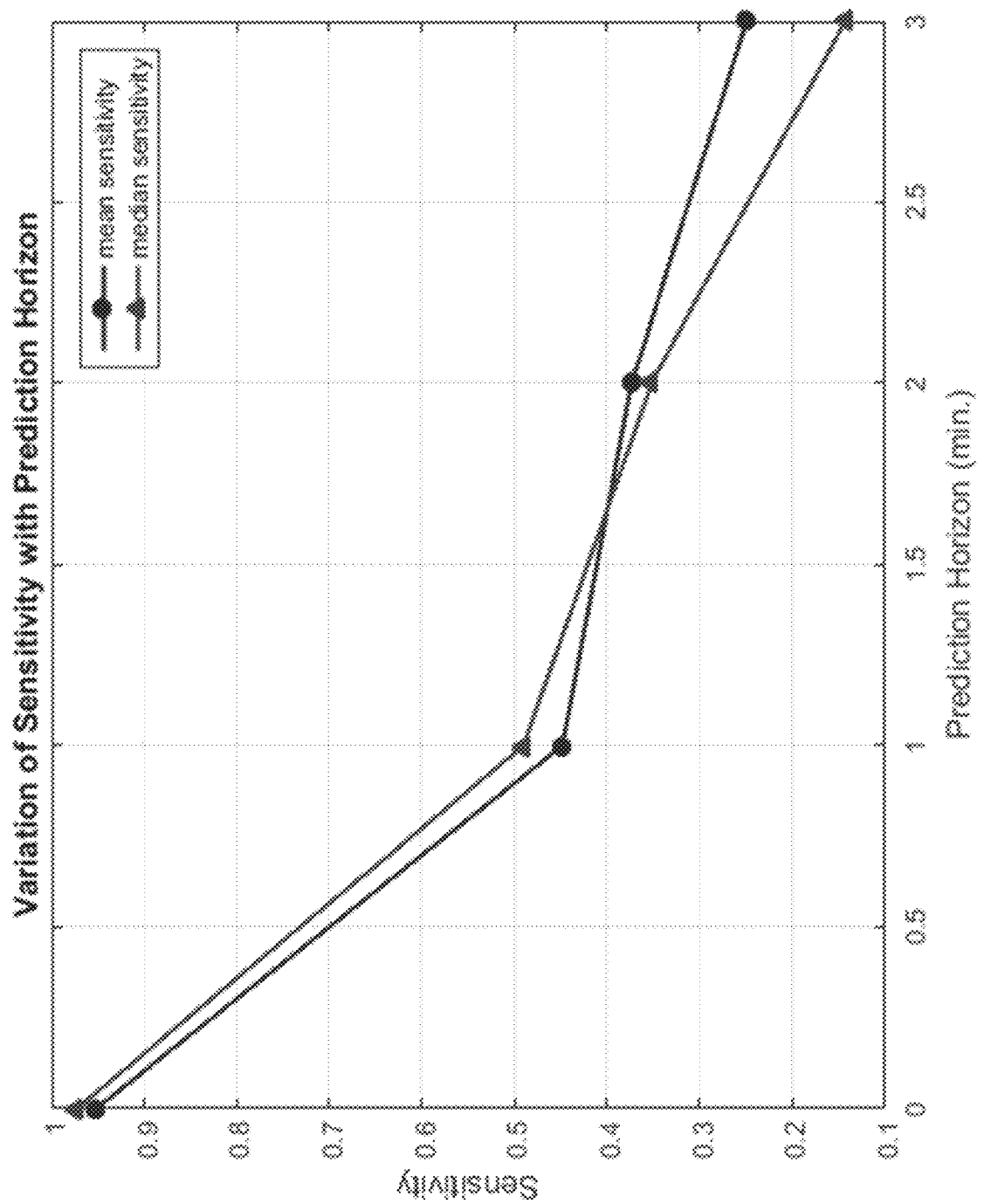
FIG. 4 is a graphical illustration depicting variation of mean and median classification sensitivity with prediction horizon for all patients/records.

The results indicate that sensitivity is above 85% for almost all patients when the SVM performs classification between ECGs that terminate right at an AF episode and ECGs belonging to the distant class. As shown in FIG. 4, sensitivity tends to drop on average as the prediction horizon increases, and ECGs further away from the episode make up the pre-AF class. The occasional small increases in sensi- 640 and are positioned on a back surface of the housing 640 to establish contact with the skin of a patient. The other Z-axis electrode 630 is connected to the device 600 by an external wire and is placed on the back (or other suitable location) of the human body, as previously described. This single external Z-axis electrode 630 may be held in place using a bandage, strap or any other device designed to hold the electrode 630 in place on the patient's back. In one embodiment of the invention, the wire and single Z-axis electrode 630 may be integrated within a strap, such as a single strap, that can be securely fastened around the patient's chest and back. Thus, the number of wires required to monitor a patient's individual cardiac rhythm is significantly reduced over the current 12-lead ECG machines. Using a strap to hold the electrode 630 for the Z-axis in place can be used for ambulatory, in-patient and out-patient monitoring allowing for greater comfort and mobility for the patient.

The integrated VCG device 600 may further include analog processing circuitry 645. The analog processing circuitry receives the signals on the six (6) X, Y and Z leads and may pass the signals through a differential amplifier and subsequently through a band-pass filter to remove high frequency noise. The amplified and filtered signals may then be passed through a buffer amplifier of the analog processing circuitry 645 to optimally match impedance with an analog-to-digital (A/D) converter 660. As such, the amplified, band-pass signals are converted into high-resolution digital data at the A/D converter 650. In this embodiment of FIG. 6, the analog-to-digital converter 650 is integrated into the integrated VCG device 640.

Following the conversion of the analog signals acquired by the electrodes to digital data at the A/D converter 650, the digital data may be stored in a memory and/or transmitted to a digital signal processor 655 for further processing. The digital signal processor 655 may include hardware and software for performing various signal processing functions, such as removal of residual 60 Hz power-line noise, adaptive filtering functions to recalibrate and re-orthogonalize the electrodes and transformation of the 3-lead VCG signal data to a 12-lead ECG.

The integrated VCG device 600 may further include telemetry circuitry 660, which may be embodied as a wireless transmission protocol. The telemetry circuitry 660 may receive the digital data from the digital signal processor 655 and may wirelessly transmit the digital data to a personal device or to a server 680. In a particular embodiment, the telemetry circuitry 660 may be a wireless communication system using an appropriate wireless protocol (e.g., Bluetooth®, Bluetooth® low-energy, ZigBee, WiFi, etc.) that receives the processed data from the digital signal processor 255 and transmits the integrated VCG device 600 information, diagnoses, data analysis reports, etc. through an internal antenna 690. Considering a sampling rate of 1 KHz, and a 12-bit analog-to-digital converter, a nominal bit rate of 36 Kbps may be suitable for transmitting the three VCG signals, although other rates are within the scope of the present invention. Such a data rate, along with the necessary protocol and control and management overhead, can easily be accommodated by a Bluetooth® low-energy wireless module that can support rates up to 1 Mbps. In order to provide security between two communicating entities, the protocol may be used to provide encryption and authentication. The receiver of this data can be any unit desired by the user, for example an electronic device (e.g., computer, smartphone, tablet, hand-held device) connected wirelessly, a hospital server connected through a Wireless Local Area Network (WLAN), a cellular network or a combination of devices. Upon transfer of the integrated VCG information to the electronic device, the electronic device can monitor the information in real-time and/or use the information for further processing. In addition, the external integrated VCG device 600 can also exchange intelligent information with a pacemaker or other implantable Cardioverter/Defibrillator device 685.

The integrated VCG device 600 may further include a microcontroller 670 in communication with the analog processing circuitry, the A/D converter 250, the digital signal processor and associated memory 655 and the telemetry circuitry 660. The microcontroller is in communication with the digital signal processor 655 and may be configured to drive the user interface/display 665 that can be used to query the integrated VCG system for information/diagnoses, to adjust settings, to reprogram the system and to toggle between various modes (e.g., 6-lead mode, sleep mode, ICU mode, training mode, etc.).

Additionally, the digital signal processor 655 and microcontroller 670, and/or associated circuitry, will also contain a trainable learning system that analyzes the VCG data, learns various VCG patterns, and outputs useful information and diagnoses for the patient. As such, in accordance with the present invention the VCG device 600 may be configured to identifying one or more AF (atrial fibrillation) rhythms in historical ECG data of a patient. The analog processor 645 and associated memory 655 may be configured for distinguishing between one or more distant-AF (atrial fibrillation) ECG epochs in the historical ECG data and one or more pre-AF ECG epochs in the historical data, wherein the distant-AF ECG epochs are located far away from the one or more AF rhythms in the historical ECG data and wherein the pre-AF ECG epochs are located just prior to the onset of the one or more AF rhythms in the historical ECG data, establishing a baseline for the patient based upon the one or more pre-AF ECG epochs and the one or more distant-AF ECG epochs, monitoring current electrical activity of the patient's heart using an electrical activity heart monitoring device and comparing the current electrical activity of the patient's heart to the baseline established for the patient to predict an onset of AF in the patient.

The present invention may be embodied on various computing platforms that perform actions responsive to software-based instructions and most particularly on touch-screen portable devices. The following provides an antecedent basis for the information technology that may be utilized to enable the invention.

The computer readable medium described in the claims below may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any non-transitory, tangible medium that can contain, or store a program for use by or in connection with an instruction execution system, apparatus, or device.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wire-line, optical fiber cable, radio frequency, etc., or any suitable combination of the foregoing. Computer program code for carrying out operations for aspects of the present invention may be written in any combination of one or more programming languages, including an object oriented programming language such as Java, C #, C++, Visual Basic or the like and conventional procedural programming languages, such as the "C" programming language or similar programming languages.

Aspects of the present invention are described below with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

It should be noted that when referenced, an "end-user" is an operator of the software as opposed to a developer or author who modifies the underlying source code of the software. For security purposes, authentication means identifying the particular user while authorization defines what procedures and functions that user is permitted to execute.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method comprising:
at one or more computing devices comprising one or more hardware processors and memory storing one or more computer programs executed by the one or more hardware processors to perform the method, performing the operations of:
identifying one or more AF (atrial fibrillation) rhythms in historical ECG data of a patient;
utilizing heart beat annotations in the historical ECG data to extract one or more distant-AF RR-interval time series from one or more distant-AF ECG epochs, wherein the one or more distant-AF ECG epochs are located far away from the one or more AF rhythms in the historical ECG data;
utilizing heart beat annotations to extract one or more pre-AF RR-interval time series from one or more pre-AF ECG epochs, wherein the one or more pre-AF ECG epochs are located just prior to the onset of the one or more AF rhythms in the historical ECG data;
for each of the one or more distant-AF RR-interval time series, identifying distinguishing features comprising autoregressive coefficients that capture a variation within the distant-AF RR-interval time series;
for each of the one or more pre-AF RR-interval time series, identifying distinguishing features comprising autoregressive coefficients that capture a variation within the pre-AF RR-interval time series;
distinguishing between one or more distant-AF ECG epochs in the historical ECG data and one or more pre-AF ECG epochs in the historical data based upon the distinguishing features comprising autoregressive coefficients that capture a variation within the distant-AF RR-interval time series and the distinguishing features comprising autoregressive coefficients that capture a variation within the pre-AF RR-interval time series in the historical ECG data;
training one or more classifiers to predict a future onset of AF in the patient at one or more prediction horizons based upon the one or more pre-AF ECG epochs and the one or more distant-AF ECG epochs;
monitoring current electrical activity of the patient's heart using an electrical activity heart monitoring device;
predicting a future onset of AF in the patient at one or more prediction horizons using the one or more trained classifiers and the current electrical activity of the patient's heart;
providing, by the electrical activity heart monitoring device, a warning of the predicted future onset of AF in the patient at the one or more prediction horizons; and
controlling, by the electrical activity heart monitoring device, a patient's pacemaker to regulate signals to the patient's heart in response to the warning of the predicted future onset of AF in the patient at the one or more prediction horizons.

2. The method of claim 1, wherein identifying the one or more AF rhythms in the historical ECG data of the patient further comprises identifying a plurality of distinguishing features in the historical ECG data by identifying variations in the patient's heart rate from the historical ECG data.

3. The method of claim 1, wherein identifying the one or more AF rhythms in the historical ECG data of the patient further comprises identifying a plurality of distinguishing features by:
  subtracting a cubic spline interpolated trend line from the distant-AF RR-interval time series to center the RR-interval time series about zero to generate a normalized distant-AF RR-interval time series;
  subtracting a cubic spline interpolated trend line from the pre-AF RR-interval time series to center the pre-AF RR-interval time series about zero to generate a normalized pre-AF RR-interval time series;
  for each of the one or more normalized distant-AF RR-interval time series, identifying distinguishing features in the one or more distant-AF RR-interval time series comprising, a number of outliers, a maximum, a minimum, a mean and a median; and
  for each of the one or more normalized pre-AF RR-interval time series, identifying distinguishing features in the one or more normalized distant-AF RR-interval time series comprising, a number of outliers, a maximum, a minimum, a mean and a median.

4. The method of claim 1, wherein identifying the one or more AF rhythms in the historical ECG data of the patient further comprises identifying a plurality of distinguishing features by:
  extracting one or more outliers from the one or more distant-AF RR-interval time series and extracting one or more outliers from the one or more pre-AF RR-interval time series;
  for each of the one or more distant-AF RR-interval time series, identifying distinguishing features of the one or more distant-AF RR-interval time series without the one or more outliers comprising, a median and a root mean square value; and
  for each of the one or more pre-AF RR-interval time series, identifying distinguishing features of the one or more pre-AF RR-interval time series without the one or more outliers comprising, a median and a root mean square value.

5. The method of claim 1, wherein the one or more prediction horizons are selected from 0 minutes, 1 minute, 2 minutes and 3 minutes.

6. The method of claim 1, wherein identifying the one or more AF rhythms in the historical ECG data of the patient further comprises identifying a plurality of distinguishing features by:
  identifying one or more abnormal heart beats or abnormal heart rhythm changes in the historical ECG data; and
  identifying distinguishing features comprising a number of abnormal heart beats or abnormal heart rhythm changes.

7. The method of claim 6, wherein the abnormal heart beats are selected from premature atrial contractions and premature ventricular contractions.

8. The method of claim 6, wherein the abnormal heart rhythm changes are selected from sinus bradycardia, ventricular tachycardia, atrial bigeminy, supraventricular tachycardia and ventricular bigeminy.

9. The method of claim 1, wherein identifying the one or more AF rhythms in the historical ECG data of the patient further comprises identifying a plurality of distinguishing features in the historical ECG data and wherein the plurality of distinguishing features in the historical ECG data are selected from a feature vector comprising twenty-seven values for each pre-AF ECG epoch and each distant-AF ECP epoch using a ranksum test resulting in four distinguishing features.

10. The method of claim 1, wherein each of the pre-AF ECG epochs are located less than about 3 minutes prior to the one or more AF rhythms in the historical ECG data.

11. The method of claim 1, wherein each of the distant-AF ECG epochs are located at least about 10 minutes prior to the one or more AF rhythms in the historical ECG data.

12. The method of claim 1, wherein the distant-AF ECG epoch and the pre-AF ECG epoch comprises a duration of about two minutes.

13. The method of claim 1, wherein monitoring current electrical activity of the patient's heart is performed by an embedded vectorcardiogram device.

14. A system comprising:
  analog processing circuitry and associated memory for;
    identifying one or more AF (atrial fibrillation) rhythms in historical ECG data of a patient;
    utilizing heart beat annotations in the historical ECG data to extract one or more distant-AF RR-interval time series from one or more distant-AF ECG epochs, wherein the one or more distant-AF ECG epochs are located far away from the one or more AF rhythms in the historical ECG data;
    utilizing heart beat annotations to extract one or more pre-AF RR-interval time series from one or more pre-AF ECG epochs, wherein the one or more pre-AF ECG epochs are located just prior to the onset of the one or more AF rhythms in the historical ECG data;
    for each of the one or more distant-AF RR-interval time series, identifying distinguishing features comprising autoregressive coefficients that capture a variation within the distant-AF RR-interval time series;
    for each of the one or more pre-AF RR-interval time series, identifying distinguishing features comprising autoregressive coefficients that capture a variation within the pre-AF RR-interval time series;
    distinguishing between one or more distant-AF ECG epochs in the historical ECG data and one or more pre-AF ECG epochs in the historical data based upon the distinguishing features comprising autoregressive coefficients that capture a variation within the distant-AF RR-interval time series and the distinguishing features comprising autoregressive coefficients that capture a variation within the pre-AF RR-interval time series in the historical ECG data;
    training one or more classifiers to predict a future onset of AF in the patient at one or more prediction horizons based upon the one or more pre-AF ECG epochs and the one or more distant-AF ECG epochs;
  an electrical activity heart monitoring device coupled to the analog processing circuitry and associated memory, the electrical activity heart monitoring device for;
    monitoring current electrical activity of the patient's heart;
    predicting, by the analog processing circuitry and associated memory, a future onset of AF in the patient at one or more prediction horizons using the one or more trained classifiers and the current electrical activity of the patient's heart;
    providing, by the electrical activity heart monitoring device, a warning of the predicted future onset of AF in the patient at the one or more prediction horizons; and a patient's pacemaker coupled to the electrical activity heart monitoring device, the patient's pacemaker configured to regulate signals to the patient's heart in response to the warning of the predicted future onset of AF in the patient at the one or more prediction horizons.

15. The system of claim 14, wherein identifying the one or more AF rhythms in the historical ECG data of the patient further comprises identifying a plurality of distinguishing features in the historical ECG data by identifying variations in the patient's heart rate from the historical ECG data.

16. One or more tangible non-transitory computer-readable media having computer-executable instructions for performing a method of running a software program on a computing device, the computing device operating under an operating system, the method including issuing instructions from the software program comprising:
- identifying one or more AF (atrial fibrillation) rhythms in historical ECG data of a patient;
- utilizing heart beat annotations in the historical ECG data to extract one or more distant-AF RR-interval time series from one or more distant-AF ECG epochs, wherein the one or more distant-AF ECG epochs are located far away from the one or more AF rhythms in the historical ECG data;
- utilizing heart beat annotations to extract one or more pre-AF RR-interval time series from one or more pre-AF ECG epochs, wherein the one or more pre-AF ECG epochs are located just prior to the onset of the one or more AF rhythms in the historical ECG data;
- for each of the one or more distant-AF RR-interval time series, identifying distinguishing features comprising autoregressive coefficients that capture a variation within the distant-AF RR-interval time series;
- for each of the one or more pre-AF RR-interval time series, identifying distinguishing features comprising autoregressive coefficients that capture a variation within the pre-AF RR-interval time series;
- distinguishing between one or more distant-AF ECG epochs in the historical ECG data and one or more pre-AF ECG epochs in the historical data based upon the distinguishing features comprising autoregressive coefficients that capture a variation within the distant-AF RR-interval time series and the distinguishing features comprising autoregressive coefficients that capture a variation within the pre-AF RR-interval time series in the historical ECG data;
- training one or more classifiers to predict a future onset of AF in the patient at one or more prediction horizons based upon the one or more pre-AF ECG epochs and the one or more distant-AF ECG epochs;
- monitoring current electrical activity of the patient's heart using an electrical activity heart monitoring device;
- predicting a future onset of AF in the patient at one or more prediction horizons using the one or more trained classifiers and the current electrical activity of the patient's heart;
- providing, by the electrical activity heart monitoring device, a warning of the predicted future onset of AF in the patient at the one or more prediction horizons; and
- controlling, by the electrical activity heart monitoring device, a patient's pacemaker to regulate signals to the patient's heart in response to the warning of the predicted future onset of AF in the patient at the one or more prediction horizons.

17. The media of claim 16, further comprising regulating signals to the patient's heart from a patient's pacemaker coupled to the electrical activity heart monitoring device in response to the warning of the predicted future onset of AF in the patient at the one or more prediction horizons.

18. The media of claim 16, wherein identifying the one or more AF rhythms in the historical ECG data of the patient further comprises identifying a plurality of distinguishing features in the historical ECG data by identifying variations in the patient's heart rate from the historical ECG data.

* * * * *